(12) United States Patent
Bailey et al.

(10) Patent No.: US 9,597,103 B2
(45) Date of Patent: Mar. 21, 2017

(54) ULTRASOUND BASED METHOD AND APPARATUS FOR STONE DETECTION AND TO FACILITATE CLEARANCE THEREOF

(71) Applicant: University of Washington through its Center for Commercialization, Seattle, WA (US)

(72) Inventors: Michael Bailey, Seattle, WA (US); John Kucewicz, Seattle, WA (US); Barbrina Dunmire, Burien, WA (US); Neil Owen, Seattle, WA (US); Bryan Cunitz, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/941,276

(22) Filed: Nov. 13, 2015

(65) Prior Publication Data
US 2016/0082291 A1    Mar. 24, 2016

Related U.S. Application Data

(63) Continuation of application No. 13/092,811, filed on Apr. 22, 2011, now Pat. No. 9,204,859.
(Continued)

(51) Int. Cl.
*A61N 7/02* (2006.01)
*A61B 17/225* (2006.01)
(Continued)

(52) U.S. Cl.
CPC .............. *A61B 17/225* (2013.01); *A61B 6/03* (2013.01); *A61B 6/485* (2013.01); *A61B 8/085* (2013.01); *A61B 8/488* (2013.01); *A61B 17/2256* (2013.01); *A61N 7/00* (2013.01); *A61B 5/055* (2013.01); *A61B 5/7232* (2013.01); *A61B 2017/22005* (2013.01);
(Continued)

(58) Field of Classification Search
USPC ............................................................ 600/1
See application file for complete search history.

(56) References Cited

U.S. PATENT DOCUMENTS

| 4,907,572 A | 3/1990 | Borodulin et al. |
| 4,962,754 A | 10/1990 | Okazaki |

(Continued)

FOREIGN PATENT DOCUMENTS

WO    2006060492    1/2006

OTHER PUBLICATIONS

Shabana, et al. (2009) "Comparison between color doppler twinkling artifact and acoustic shadowing for renal calculus detection: an in vitro study," Ultrasound in Medicine and Biology, 35(2): 339-350.
(Continued)

*Primary Examiner* — Joel F Brutus
(74) *Attorney, Agent, or Firm* — Christensen O'Connor Johnson Kindness PLLC

(57) ABSTRACT

Described herein are methods and apparatus for detecting stones by ultrasound, in which the ultrasound reflections from a stone are preferentially selected and accentuated relative to the ultrasound reflections from blood or tissue. Also described herein are methods and apparatus for applying pushing ultrasound to in vivo stones or other objects, to facilitate the removal of such in vivo objects.

20 Claims, 15 Drawing Sheets

Related U.S. Application Data

(60) Provisional application No. 61/326,904, filed on Apr. 22, 2010, provisional application No. 61/474,002, filed on Apr. 11, 2011.

(51) Int. Cl.
*A61B 8/08* (2006.01)
*A61N 7/00* (2006.01)
*A61B 6/03* (2006.01)
*A61B 6/00* (2006.01)
A61B 5/055 (2006.01)
A61B 17/22 (2006.01)
G01S 7/52 (2006.01)
G01S 15/89 (2006.01)
A61B 5/00 (2006.01)

(52) U.S. Cl.
CPC . *A61B 2090/378* (2016.02); *A61N 2007/0004* (2013.01); *A61N 2007/0052* (2013.01); *A61N 2007/0082* (2013.01); *G01S 7/52071* (2013.01); *G01S 15/899* (2013.01)

(56) References Cited

U.S. PATENT DOCUMENTS

| | | |
|---|---|---|
| 5,048,527 A | 9/1991 | Okazaki |
| 5,059,200 A | 10/1991 | Tulip |
| 5,065,763 A | 11/1991 | Green et al. |
| 5,240,005 A | 8/1993 | Viebach |
| 5,425,366 A | 6/1995 | Reinhardt et al. |
| 6,123,679 A | 9/2000 | Lafaut et al. |
| 6,206,843 B1 | 3/2001 | Iger et al. |
| 6,385,474 B1 | 5/2002 | Rather et al. |
| 6,716,184 B2 | 4/2004 | Vaezy et al. |
| 6,728,567 B2 | 4/2004 | Rather et al. |
| 7,273,458 B2 | 9/2007 | Prausnitz et al. |
| 7,456,019 B2 | 11/2008 | Goodwin et al. |
| 7,485,101 B1 | 2/2009 | Faragalla |
| 8,038,616 B2 | 10/2011 | Angelsen et al. |
| 8,057,408 B2 | 11/2011 | Cain et al. |
| 2002/0065466 A1 | 5/2002 | Rather et al. |
| 2003/0028111 A1 | 2/2003 | Vaezy et al. |
| 2004/0006288 A1 | 1/2004 | Spector |
| 2004/0024315 A1 | 2/2004 | Chalana et al. |
| 2004/0059265 A1 | 3/2004 | Candy et al. |
| 2004/0059319 A1 | 3/2004 | Bohris |
| 2006/0052699 A1 | 3/2006 | Angelsen et al. |
| 2006/0240550 A1 | 10/2006 | Goodwin et al. |
| 2008/0146908 A1 | 6/2008 | Wu |
| 2009/0177085 A1 | 7/2009 | Maxwell et al. |
| 2009/0227992 A1 | 9/2009 | Nir |
| 2009/0230822 A1 | 9/2009 | Kushculey et al. |
| 2009/0230823 A1 | 9/2009 | Kushculey et al. |
| 2009/0275866 A1 | 11/2009 | Gelbart |
| 2009/0299187 A1 | 12/2009 | Bailey et al. |
| 2010/0256534 A1 | 10/2010 | Lacoste et al. |
| 2011/0263967 A1 | 10/2011 | Bailey et al. |
| 2013/0303906 A1 | 11/2013 | Cain et al. |

OTHER PUBLICATIONS

Rosenschein, et al. (2000) "Ultrasound imaging-guided noninvasive ultrasound thrombolysis: preclinical results," Circulation, 102(2): 238-245.

Albala, et al.: Lower Pole I: A Prospective Randomized Trial of Extracorporeal Shock Wave Lithotripsy and Nephrostolithotomy for Lower Pole Nephrolithiasis—Initial Results. The Journal of Urology, 166: 2072, 2001.

Pearle, et al: Prospective Randomized Trial Comparing Shock Wave Lithotripsy and Ureteroscopy for Lower Pole Caliceal Calculi 1 cm or Less. The Journal of Urology, 179: S69, 2008.

Chen, et al.: Extracorporeal Shock Wave Lithotripsy for Lower Pole Calculi: Long-term Radiographic and Clinical Outcome. The Journal of Urology, 156: 1572, 1996.

Sampaio, et al.: Limitations of extracorporeal shockwave lithotripsy for lower caliceal stones: anatomic insight. J Endourol, 8: 241, 1994.

Chiong, et al.: Randomized controlled study of mechanical percussion, diuresis, and inversion therapy to assist passage of lower pole renal calculi after shock wave lithotripsy. Urology, 65: 1070, 2005.

Kekre, et al.: Optimizing the fragmentation and clearance after shock wave lithotripsy. Curr Opin Urol, 18: 205, 2008.

Pace, et al.: Mechanical percussion, inversion and diuresis for residual lower pole fragments after shock wave lithotripsy: a prospective, single blind, randomized controlled trial. J Urol, 166: 2065, 2001.

International Search Report for PCT/US2011/033652, mailed Dec. 12, 2011.

O'Brien, Jr. et al, The Risk of Exposure to Diagnostic Ultrasound in Postnatal Subjects Thermal Effects, J Ultrasound Med, 2008, 517-535, 27.

Heimdal, Ultrasound Doppler Measurements of Low Velocity Blood Flow: Limitations Due to Clutter Signals from Vibrating Muscles, IEEE Transaction Ultrasonics Ferroelectronics, and Frequency Control, 1997, pp. 873-881, vol. 44.

Jensen, Stationary Echo Canceling in Velocity Estimation by Time-Domain Cross-Correlation, IEEE Transactions on Medical Imaging, No. 3, 1993, pp. 471-477, vol. 12.

Kim, et al., Color Doppler Twinkling Artifacts in Various Conditions During Abdominal and Pelvic Sonography, J Ultrasound Med., 2010, 621-632, American Institute of Ultrasound in Medicine.

Chelfouh, et al., Characterization of Urinary Calculi: In Vitro Study of Twinkling Artifact Revealed by Color-Flow Sonography, AJR, Oct. 1998, 1055-1060, ARRS, 171.

Khan, et al., "Twinkling Artifact on Intracerebral Color Doppler Sonography", AJNR Am J. Neuroradiol 20: Feb. 1999, pp. 246-247.

Riccabona, Michael, "Potential of Modern Sonographic Techniques in Pediatric Uroradiology", European Journal of Radiology 43, 2002, pp. 11 0-121.

Krings, et al., "Extracorporeal Shock Wave Lithotripsy Retreatment (Stir-Ur) Promotes Discharge of Persistent Caliceal Stone Fragments After Primary Extracorporeal Shock Wave Lithotripsy", The Journal of Urology, 1992, vol. 148, 1040-1042.

Parr, et al., "Does Further Extracorporeal Lithotripsy Promote Clearance of Small Residual Fragments?", British Journal of Urology, 1991, 68, 565-567.

Shah, et al., "Novel ultrasound method to reposition kidney stones", Urol Res, 2010, 38:491-495.

(a)

(b)

ULTRASOUND BASED METHOD AND APPARATUS FOR STONE DETECTION AND TO FACILITATE CLEARANCE THEREOF

RELATED APPLICATIONS

This application is a continuation of U.S. patent application Ser. No. 13/092,811 filed Apr. 22, 2011, which claims priority from U.S. Provisional patent application 61/326,904 filed Apr. 22, 2010, and from U.S. Provisional patent application 61/474,002 filed Apr. 11, 2011, each of which are incorporated herein by reference in their entireties.

GOVERNMENT RIGHTS

This invention was made with government support under grant numbers DK043881 and DK086371 awarded by the National Institutes of Health and SMST01601 awarded by the National Space Biomedical Research Institute. The government has certain rights in the invention.

BACKGROUND

Residual stone fragments such as kidney stones often remain after current methods for stone treatment, such as extracorporeal shockwave lithotripsy, ureteroscopic lithotripsy, and percutaneous nephrolithotomy. In some cases such fragments remain in the lower pole of the kidney. New stones may grow from these fragments, and such fragments have been reported to contribute to a 50% recurrence of kidney stones within 5 years. Thus, improved methods for detecting stones and for facilitating stone clearance from the body are needed.

SUMMARY

It is thus one object of the invention to provide an ultrasound detection method and system for stones in a mammal in which ultrasound reflections from stones are selected and displayed preferentially relative to ultrasound reflections from blood or other tissue.

It is another object of the invention to provide an ultrasound detection method and system for stones in a mammal in which ultrasound reflections from stones are selected and displayed preferentially relative to ultrasound reflections from blood or other tissue, wherein the applied ultrasound used for stone detection is B-mode ultrasound.

It is another object of the invention to provide an ultrasound detection method and system for stones in a mammal in which ultrasound reflections from stones are selected and displayed preferentially relative to ultrasound reflections from blood or other tissue, wherein the applied ultrasound used for stone detection is Doppler ultrasound.

It is another object of the invention to provide an ultrasound detection method and system for stones in a mammal in which ultrasound reflections from stones are selected and displayed preferentially relative to ultrasound reflections from blood or other tissue, wherein the applied ultrasound used for stone detection is Doppler ultrasound, and the preferentially selected reflections are those associated with the Doppler ultrasound twinkling artifact.

It another object of the present invention to apply an ultrasonic pushing force to an in vivo stone in a mammal to facilitate clearance.

It is another object of the present invention to apply an ultrasonic pushing force to a stone to facilitate clearance while using detection of the stone.

It is another object of the present invention to apply an ultrasonic pushing force to a stone to facilitate clearance while using ultrasonic detection of the stone.

In accordance with one aspect of the present invention, ultrasound is used to apply a pushing force to a stone in vivo to facilitate clearance, without causing undue damage to the surrounding tissue. The applied pushing ultrasound can be of lower pressure amplitude than ultrasound used in shock wave lithotripsy ("swl"). It also can have a higher duty cycle to create a sustained force that can reposition a stone.

In another aspect of the present invention, the pushing ultrasound is applied in conjunction with detection ultrasound, to allow for detection of the stone such as by visualization on an ultrasound display monitor, or by aural detection. In one embodiment, the detection ultrasound may be a variant of B-mode ultrasound; in another embodiment the detection ultrasound may be a variant of Doppler ultrasound. In a preferred embodiment of the invention, the ultrasound reflections from the stones are selected and displayed preferentially relative to ultrasound reflections from blood and tissue. Where Doppler ultrasound is used, in one embodiment of the invention the twinkling artifact can be used to facilitate detection of the stone. In one aspect of the invention, such detection ultrasound is used to locate a stone prior to the application of the pushing ultrasound. In another aspect of the invention, the detection ultrasound is used in real time to monitor the movement of the stone during the application of the pushing ultrasound.

In one embodiment of any aspect of the present invention, the pushing ultrasound is applied as a focused beam directed along a propagation axis directed to one or more stones or fragments. In another embodiment of any aspect of the invention the pushing ultrasound is applied in an unfocused or weakly focused mode to a general region of anatomy where stones are likely to occur. For example, such unfocused or weakly focused ultrasound energy could be applied generally to a region of a kidney such as the lower pole region to stir up any fragments that might be located therein, thereby facilitating clearance.

In one embodiment of the invention the methods and systems are used to facilitate the removal of stones, such as stones ranging from about 1 to about 10 mm in diameter. In another embodiment, the in vivo stone is fragmented before applying the pushing ultrasound. Such fragmenting can be carried out by any suitable technique, including but not limited to extracorporeal shockwave lithotripsy, ureteroscopic lithotripsy, and percutaneous nephrolithotomy. In another embodiment of any aspect of the invention, the in vivo stone is fragmented after applying the pushing ultrasound, wherein the in vivo stone can be first pushed toward an exit, so that once fragmented, the fragments are more likely to be easily cleared. In another embodiment of the invention, pushing ultrasound is used to induce displacement of stones that may be larger than 10 mm in diameter. For example, displacement of larger stones at the entrance to the ureteropelvic junction (UPJ) would have considerable clinical benefit in relieving pain.

In an exemplary embodiment of the invention for facilitating removal of in vivo stones, detection ultrasound is used to locate the in vivo stone, and pushing ultrasound is used to cause the located in vivo stone to move toward an exit, which exit can be either naturally occurring or provided surgically.

In a further embodiment, the step of using pushing ultrasound to cause the in vivo stone to move is implemented using a quantity of pushing ultrasound sufficient to cause the in vivo stone to move at a rate of at least about one centimeter per second.

In another embodiment, the pushing ultrasound has a pulse duration of about one hundred times that of the detection ultrasound.

In another aspect of the invention the amount of pushing ultrasound used is calculated based on a numerical simulation program, such that ultrasound exposures can be determined for each unique stone and anatomical situation. In such calculations the radiation force on the stone is found using elasticity equations based on the predicted in situ parameters of ultrasound field and expected mechanical properties of the stone, such as density, shear and compressional moduli.

In a further aspect, the present invention provides non-transitory computer readable storage media, for automatically carrying out the methods of the invention on a device, such as an ultrasound device or system according to the invention.

In a further aspect, the system of the present invention displays the stone as it is pushed in real time and tracks the stone motion, continually refocusing the pushing force on the moving stone.

This Summary has been provided to introduce a few concepts in a simplified form that are further described in detail below in the Detailed Description of the Invention. However, this Summary is not intended to limit key or essential features of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates a first exemplary embodiment employing the concepts disclosed herein, wherein detection ultrasound is used to locate an in vivo object, and pushing ultrasound is used to move the in vivo object in a desired direction while detecting the movement of the object;

FIG. 2 schematically illustrates an exemplary system employed to visualize an in vivo object using detection ultrasound, and to move the in vivo object, using pushing ultrasound;

FIG. 3 is a flow chart of exemplary steps employed to visualize an in vivo object using detection ultrasound, and to move the in vivo object, using pushing ultrasound;

FIG. 4 schematically illustrates an empirical system employed to verify that pushing ultrasound can be used to move an in vivo object, and that such motion can be visualized in real-time;

FIG. 5A illustrates the basic components of a system for practicing the invention; B is a schematic illustration of ultrasound radiation emanating from and being reflected back toward a transducer; C is a flowchart of a system for B-mode ultrasound imaging in accordance with the prior art;

DETAILED DESCRIPTION OF THE INVENTION

Figure 1:
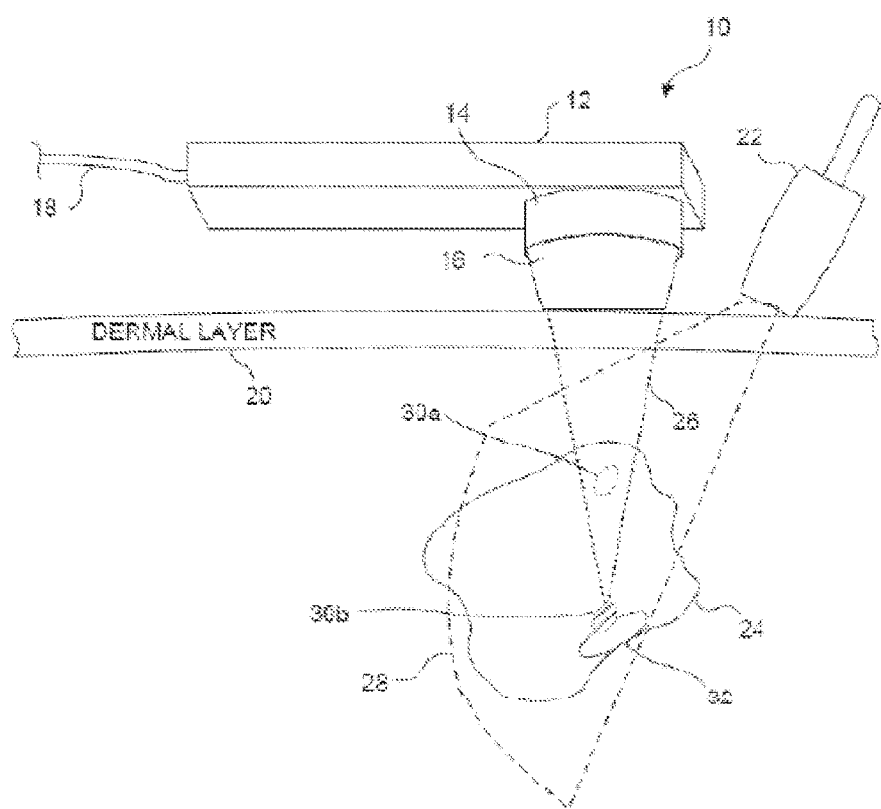

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment or aspect disclosed herein can be combined with one or more features of any other embodiment or aspect that is disclosed, unless otherwise indicated.

The following additional definitions shall apply in this application.

"Stone"—any piece of calculus material such as may be found, for example, in an organ, duct or vessel of a mammal, and including stones, stone fragments, and stone dust that may result from the application of shock waves or other therapeutic procedures; and equivalent embedded objects for which movement or displacement is desired.

Pressure amplitude—the maximum displacement of the acoustic pressure from ambient.

Duty cycle (also referred to as duty factor) —pulse duration divided by pulse repetition frequency times 100%.

Power —Energy per time, for both electric and acoustic power. Electric power excites the transducer element as a source; acoustic power is in the acoustic wave generated by the transducer element.

Intensity —power transmitted through a cross-sectional area. Cross sectional area can be determined as the beamwidth of the acoustic beam; or as applied to a stone cross sectional area can be the cross section of the stone.

Pulse—an acoustic wave of a certain duration. A single pulse encompasses one or several cycles of pressure oscillation at the center frequency. The excitation of one or more elements in the transducer generates a pulse. Pulses in B-mode tend to be 1-2 cycles and pulses in Doppler tend to be 3-7 cycles. The pulse created by a shock wave lithotripter tends to be 1 cycle.

Doppler Ultrasound—a mode or several modes of ultrasound imaging used to detect blood flow.

B-mode ultrasound—a mode of ultrasound used to create an image of anatomical structures.

Ultrasound waves can be characterized by any one or more of the following intensity parameters:

Temporal peak, $I_{TP}$, is the highest instantaneous intensity in the beam.

Temporal average, $I_{TA}$, is the time averaged intensity over the pulse repetition period.

Pulse average, $I_{PA}$, is the average intensity of the pulse.

Spatial peak, $I_{SP}$, is the highest intensity spatially in the beam.

Spatial average, $I_{SA}$, is the average intensity over the beam area.

Spatial average-temporal average intensity, $I_{SATA}$, is the acoustic power contained in the beam in watts averaged over at least one pulse repetition period, and divided by the beam area.

Spatial average-pulse average intensity, $I_{SAPA}=I_{SATA}$/duty cycle, where $I_{PA}=I_{TA}$/duty cycle.

Spatial peak-temporal average intensity, $I_{SPTA}=I_{SATA}(I_{SP}/I_{SA})$.

Spatial peak-pulse average intensity, $I_{SPPA}=I_{SATA}(I_{SP}/I_{SA})$ duty cycle.

Pushing Ultrasound

Acoustic radiation force results from the transfer of acoustic wave momentum to an absorbing or reflecting object. In the context of the present invention, acoustic radiation of selected pressure amplitude, duration, frequency, and duty cycle is applied to a stone which absorbs the momentum to facilitate non-invasive repositioning of the stone, to allow removal, passage, or further treatment. Such acoustic radiation is referred to herein as pushing ultrasound.

The pushing ultrasound of the system of the present invention will operate at $I_{SPTA}>3$ W/cm$^2$ in situ. In one preferred embodiment, the pushing ultrasound of the present invention has a time averaged spatial peak intensity of $I_{SPTA}>4$ W/cm$^2$. A higher pressure can allow for a shorter pulse time or a longer time between pulses. In some embodiments of the invention, the longer time between pulses can be used to real-time imaging between pushing pulses. This is in comparison to diagnostic ultrasound approved for use in the U.S. which must operate at $I_{SPTA}<720$ mW/cm$^2$ (and MI<1.9) and $I_{SPPA}<190$ W/cm$^2$, and shock wave lithotripsy and physical therapy ultrasound which operate at $I_{SPTA}<3$ W/cm$^2$.

Further in accordance with the present invention, pushing ultrasound waves have pressure amplitudes in the range of between about 5 MPa and about 30 MPa, preferably between about 10 MPa and 20 MPa, and most preferably between about 13 MPa and 18 MPa. As is known in the art, detection ultrasound waves generally have a pressure amplitude in the range of about 5 MPa or less, while, ultrasound waves used in shock wave lithotripsy ("swl") as approved for use in the United States have amplitudes of at least about 30 MPa as measured in water. The high pressures of lithotripsy are necessary to break the stones The pushing ultrasound waves used in the present invention also are distinguished from other ultrasound waves by the number of cycles per pulse, and by the duty cycle. B-mode ultrasound for detection and shock wave ultrasound for lithotripsy each use a single pulse per cycle; while pushing ultrasound waves used in the present invention use more than one pulse per cycle, typically more than about 5-10 pulses per cycle. Pushing ultrasound waves for use in the present invention can have a duty cycle of greater than 1%. For example, in one embodiment the pushing ultrasound waves pulse for 100 microseconds every three milliseconds. By comparison, lithotripsic ultrasound may run, for example, for a 5 microsecond pulse, with a 250 millisecond duration between pulses, for a duty cycle of <1%.

In a preferred embodiment of the invention, the pushing ultrasound will have a pulse duration of about 100 µs; a center frequency of about 2.3 MHz, a pressure amplitude of about 15 MPa in situ; with bursts repeated every 3 ms, and the total duration of each push sequence being about 1 s. In one embodiment of the invention, imaging pulses can be interleaved within the pushing pulses for real time imaging The pushing ultrasound facilitates movement of a stone; in one embodiment such movement can be toward an exit location. The exit can be a natural exit of a duct, vessel, or organ, or created surgically. The pushing ultrasound can be more focused when directed to a particular stone, or either weakly focused or unfocused if directed toward a general region of the body such as a kidney pole. For example, a kidney pole area may be suspected of containing very small stone fragments or stone dust which may be difficult to image. Such weakly focused or unfocused pushing ultrasound can be used to stir up the small fragments or dust and facilitate their removal from the pole of the kidney, without the risk of tissue injury that might be caused by shock wave lithotripsy.

In some aspects of the invention, an imaging system can be used to locate the stones for the application of pushing ultrasound. In one embodiment of the invention, such imaging can be accomplished by known imaging techniques such as fluoroscopy. In other embodiments of the invention, such imaging can be accomplished by the application of any of various modes of detection ultrasound, as discussed in greater detail below.

Detection Ultrasound

As noted above, in one aspect the inventive system and method disclosed herein employ detection ultrasound to locate stones within an organ, duct, or vessel such as the kidney, wherein the ultrasound waves reflected from a stone are preferentially selected and displayed relative to ultrasound waves reflected off blood or tissue. The detection ultrasound used in connection with the present invention can be based on B-mode ultrasound or Doppler ultrasound, or both.

Doppler ultrasound is a form of ultrasound that can detect and measure blood flow. There are several types of Doppler ultrasound. Color Doppler is a technique that estimates the average velocity of flow within a vessel by color coding the information. The direction of blood flow is assigned the color red or blue, indicating flow toward or away from the ultrasound transducer. Color Doppler can overlay color on a B-mode image. Pulsed Doppler allows a sampling volume or "gate" to be positioned in a vessel visualized on the gray-scale image, and displays a graph of the full range of blood velocities within the gate versus time. The amplitude of the signal is approximately proportional to the number of red blood cells and is indicated, not in color, but simply as a shade of gray. Power Doppler depicts the amplitude, or power, of Doppler signals rather than the velocity. This allows detection of a larger range of velocities and thus better visualization of small vessels, but at the expense of directional and velocity information.

B-mode ultrasound is based on two-dimensional diagnostic ultrasound presentation of echo-producing interfaces in a single plane. B-mode ultrasound is based on brightness modulation, in which bright dots on a screen represent echoes, and the intensity of the brightness indicates the strength of the echo. As is known in the art, the Doppler ultrasound can be overlaid on an image created by B-mode ultrasound, such as to show blood vessels which may appear as red or blue on the ultrasound display.

Standard Doppler detection such as for detecting blood flow is based on small signals that change over time, that are coherent, and have a pattern. At some point in the Doppler image processing, the signals from blood encompass a relatively narrow band of higher frequency and lower amplitude, while ultrasound reflections from tissue such as vessel walls and organ tissue encompass a relatively narrow band of lower frequency and higher amplitude. When using Doppler ultrasound to detect motion of blood, it is known in the art to use an optional "wall filter" which electronically filters from the reflected ultrasound signal the lower frequency, higher amplitude waves reflecting from the vessel walls. When using Doppler ultrasound to evaluate blood flow, it known in the art to autocorrelate data from an ensemble of Doppler pulses, frames, or volumes, in which patterns of coherent data with relatively small changes from pulse to pulse are retained and converted into an image signal, while pulse data that is not part of the coherent pattern is deleted from the signal as unwanted "noise."

Stones are strong scatterers and therefore reflect strong signals. A signal reflected from stone can change on the next pulse more than a similarly strong signal reflected from tissue. While the cause of the difference in ultrasound reflective properties is not completely understood, it is believed that this difference may be caused by the abruptness of the transition from soft tissue to hard stone, by motion of the stone, or by internal waves in the stone not present in softer tissue. Rather than deleting these signals as unwanted electronic noise as in ultrasound systems of the prior art, in the method and system of the present invention the reflected ultrasound signals are processed such that these strong signals are preferentially retained relative to the narrow bands of coherent signals reflected from blood and tissue, and the retained signals are converted into an image on a display. Thus in contrast to the prior art, the present invention detects stones as strong signals that change over time, with significant change in amplitude that randomly appears in some frames but not others. In some embodiments of the invention these acoustic differences can be exacerbated by nonlinear responses of the front end electronics of the imager.

This feature of the invention in which reflections from stones are preferentially selected and retained in an image display relative to reflections from blood or tissue can be used both with B-mode detection ultrasound and with Doppler detection ultrasound. Where the applied detection ultrasound is Doppler ultrasound, the strong signals that are preferentially selected and displayed as an image can be those reflected waves related to the "twinkling" artifact of ultrasound in which the object being scanned appears brighter or with different colors on the image display monitor.

In those embodiments of the invention in which the pushing ultrasound is used in conjunction with Doppler detection ultrasound, then it is a feature of one embodiment of the present invention that this twinkling artifact can be used to enhance visualization of the stone during the application of pushing ultrasound, thereby allowing for greater control and accuracy in directing the pushing ultrasound toward the stone to be moved. In one embodiment of the invention, an ultrasound system recognizes the twinkling artifact on an ultrasound display and redirects subsequent pulses of pushing ultrasound waves to more efficiently facilitate motion of the stone in a desired direction.

In a further aspect, the present invention provides non-transitory computer readable storage media, for automatically carrying out the methods of the invention on a device, such as an ultrasound device or system according to the invention. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by a Central Processing Unit ("CPU"). The computer readable medium includes cooperating or interconnected computer readable medium, which exist exclusively on the processing system or be distributed among multiple interconnected processing systems that may be local or remote to the processing system.

Unless the context clearly dictates otherwise, embodiments in one aspect of the invention may be used in other aspects of the invention, and can be combined with each other.

FIG. 1 illustrates an exemplary use of pushing ultrasound applied to move a kidney stone in accordance with the concepts disclosed herein. In a pushing ultrasound therapy probe 10, an acoustic coupling 16 is attached to a therapy transducer 14 that is mounted to a handle 12. A lead 18 couples the transducer 14 to a power supply (not shown). In FIG. 1, probe 10 is being used to apply pushing ultrasound to a kidney 24 through a dermal layer 20 of a patient (not otherwise shown).

Probes capable of producing and receiving both detection ultrasound and pushing ultrasound and suitable for use in the present invention include the C4-2 and P4-2 HDI scanheads commercially available from Philips/ATL, although the scope of the invention is not so limited.

While many different acoustic transducers are suitable for pushing ultrasound applications, many ultrasound transducers exhibit a generally conical-shaped beam 26. When probe 10 is positioned so that beam 26 passes through the kidney, acoustic pressure moves a kidney stone from a first position 30a to a second position 30b, closer to an exit 32 which can be either naturally present or artificially introduced such as by surgery. By properly positioning probe 10, the user can control the direction the kidney stone will move. It should be understood that in the context of an artificial exit, the concepts disclosed herein can be used to reposition stones closer to artificially placed tubes/catheters during surgery, such that the method and system disclosed herein can be used intra-operatively.

Acoustic transducer 14 can have a fixed focal length, or a variable focal length. Variable focal length transducers are generally more useful. In applications where a fixed focal length acoustic transducer is used for application of pushing ultrasound, acoustic coupling 16 can be used to control the position of focal region of beam 26 relative to the patient. If a relatively thicker acoustic coupling 16 is employed, the focal region will be disposed closer to dermal layer 20, while if a relatively thinner acoustic coupling 16 is employed, the focal region will penetrate further below the dermal layer and deeper into the subcutaneous target. Thus, the thickness of acoustic coupling 16 can be used to control the position of the focal region relative to a patient's tissue. The transducer may also be a linear, curvilinear, or phased array and be able to steer the beam to push the stone off the axis of the transducer.

In FIG. 1, an ultrasound imaging probe 22 generates an image plane 28. Focal beam 26 and the kidney stone at positions 30*a* and 30*b* lie within image plane 28, so that the movement of the kidney stone can be visualized in an ultrasound image provided by ultrasound imaging probe 22 during therapy. In other embodiments of the invention, the source of imaging ultrasound and the source of pushing ultrasound for moving the stone can be contained within a single probe housing. In still other embodiments of the invention, one transducer having one or a plurality of elements can be used to detect and push the stone. Suitable transducers include the P4-2 or C4-2 HDI transducer from ATL/Philips. These are standard curvilinear and phased array probes for imaging.

Figure 2:
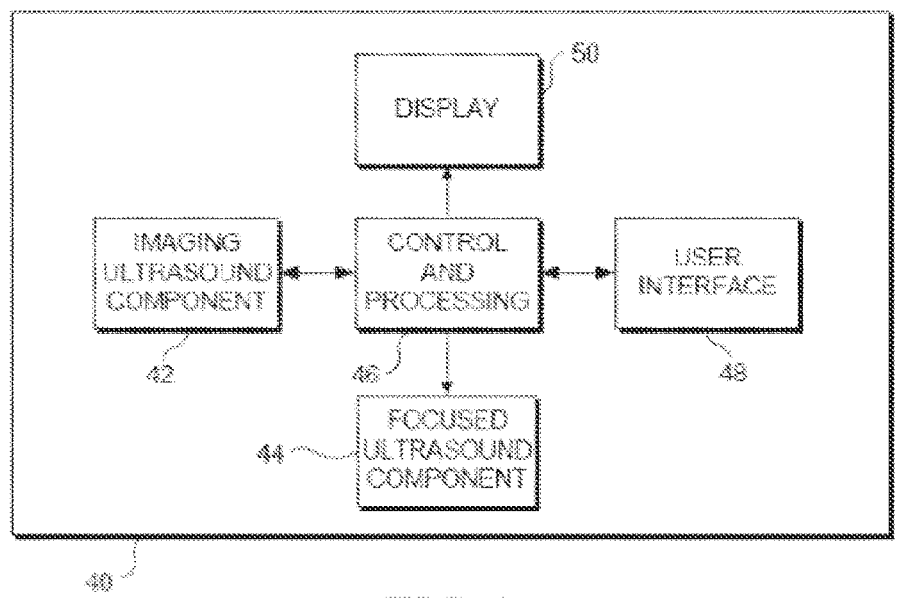

FIG. 2 is a functional block diagram of a system for detecting and pushing in vivo objects such as kidney stones and kidney stone fragments. System 40 includes a detection ultrasound component 42, a pushing ultrasound component 44, a control and processing component 46, a user interface 48, and a display 50. In other embodiments, a single unit can provide both ultrasonic detection and ultrasound treatment. Where the detection ultrasound component 42 is a Doppler ultrasound component, then detection of the stone in vivo can use the twinkling artifact in Doppler imaging. Processing and control component 46 can include the power supplies required to energize the ultrasound transducers in detection ultrasound component 42 and pushing ultrasound component 44, or such components can be implemented separately.

In one aspect of the invention the user can interact with user interface 48 to choose an area on the display on which the pushing ultrasound is to be focused. Thus the user can guide the repeated application of pushing ultrasound in real time to urge the stone toward an exit. In one aspect of the invention, the ultrasound system detects the motion of the stone and then sends a new pushing pulse to the new location, to continuously follow the stone on its movement toward an exit. User interface 48 can include a mouse or touch screen as are known in the computer and medical technology arts.

If desired, a separate processing and control component can be employed for each of detection ultrasound component 42 and pushing ultrasound component 44. Displays are sometimes incorporated into conventional detection ultrasound components, and if desired such a display can be used in place of display 50. User interface 48 is employed at least to control the pushing ultrasound component 44, enabling the operator to energize that component as required to achieve the desired movement of the in vivo object. With respect to the operation of pushing ultrasound component 42, if desired, control and processing component 46 can override a command to trigger the pushing ultrasound component if the control and processing component 46 determines that delivery of additional pushing ultrasound could undesirably damage tissue, such as may occur due to thermal or mechanical effects). The processing and control component can be implemented using a custom circuit (i.e., a hardware implementation, such as an application specific integrated circuit) or a processor executing machine instructions stored in a memory (i.e., a software implementation, where the software is executed by a computing device, such as a desktop or laptop computer). Such processing and control components are known to those of ordinary skill in the art.

Figure 3:
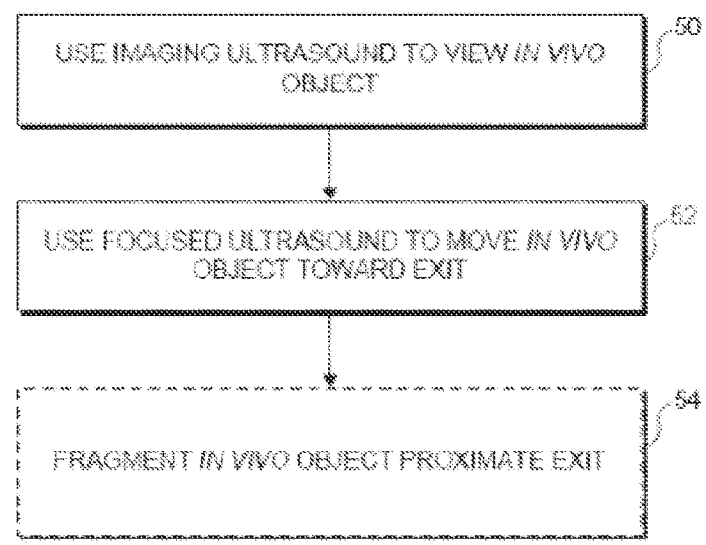

FIG. 3 is a flowchart of exemplary steps for implementing the concepts disclosed herein. In representative block 50, detection ultrasound is used to visualize an in vivo object such as a kidney stone or kidney stone fragment. As discussed above, in an exemplary but not limiting embodiment, the twinkling artifact in Doppler ultrasound is used to visualize the in vivo object. In a block 52, pushing ultrasound is used to move the in vivo object in a desired direction. In general, the desired direction will cause the in vivo object to move to a natural or artificial opening, facilitating clearance of the in vivo object. In some exemplary embodiments, the in vivo object is a fragment of a kidney stone that was previously fragmented. In other exemplary embodiments, the in vivo object is a relatively large intact kidney stone that must be fragmented prior to removal. Thus, in optional block 54, the in vivo object that has been moved closer to an exit is fragmented to facilitate its removal. Any of the known fragmentation techniques can be employed.

EXAMPLE 1

In an empirical study to test the concepts disclosed herein, a pushing ultrasound device was used to move a kidney stone fragment, with the goal of facilitating passage. In one study, natural and artificial stones about 1-8 mm in length were surgically placed in the urine space in pig kidneys. A new system was assembled and programmed to both image stones and push stones. The system had the general design of FIG. 5A where the pulser/receiver and analog to digital converter box was a Verasonics Ultrasound Engine (Verasonics, Bothell Wash.). The transducer was either a P4-2, P4-1, or C4-2 HDI transducer from ATL/Philips, Bothell Wash.).

Figure 4:
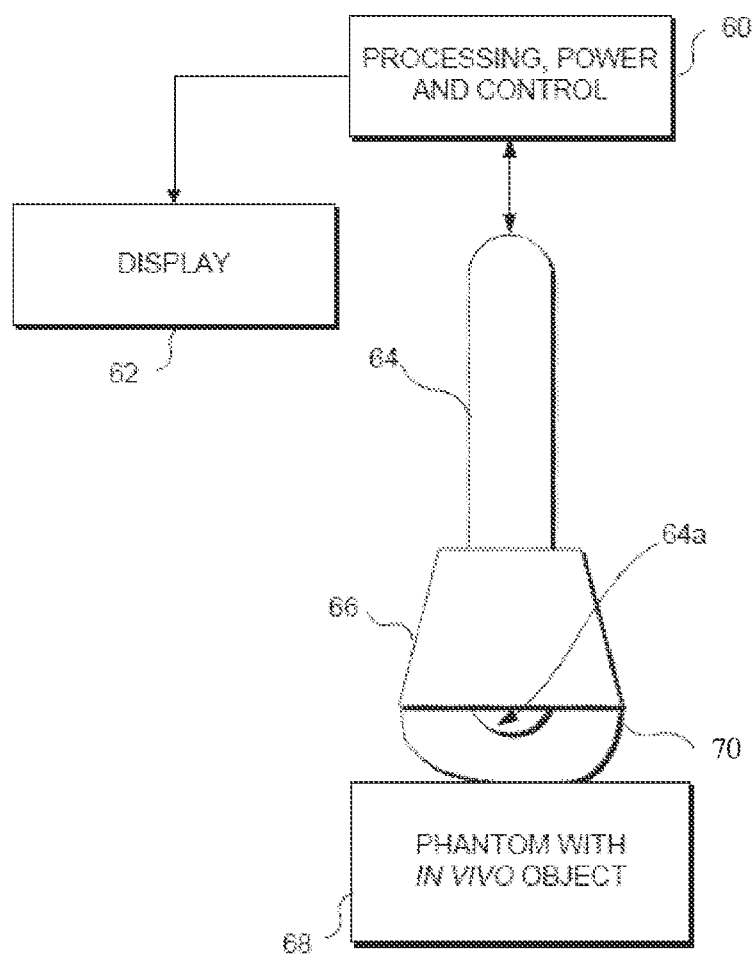

FIG. 4 schematically illustrates the setup in the empirical study. A tissue phantom 68 (or live porcine kidney) with an embedded object was provided. A pushing ultrasound component 66 was coupled to the phantom using a coupler 70. A detection ultrasound component 64 (a distal end 64*a* of which can be seen in the Figure), coaxially aligned with the pushing ultrasound component, was used to acquire images of the embedded object as it was moved in the tissue phantom/kidney by the pushing ultrasound. A processing and control component 60 was used to control the ultrasound components, and the ultrasound image was presented to the user on a display 62.

In the empirical studies, a research ultrasound device designed for other medical therapies was used, which combines a commercial ultrasound imaging system with a research pushing ultrasound therapy system. The imaging probe is placed within, looking down the axis of, the therapy probe. In the empirical study, longer bursts of higher amplitude focused ultrasound were applied than are generally employed in diagnostic ultrasound (30-ms, 10-MPa bursts repeated at 10 Hz). The force applied to stone fragments and motion of the fluid around the stone caused stone motion. Motion of natural and artificial stones was observed visually in a kidney phantom of transparent tissue mimicking gel surrounding a water-filled space, and with diagnostic ultrasound and fluoroscopy in live and excised pig kidneys.

Stone velocities were on the order of 1 cm/s and stones quickly moved out of the ultrasound focus. Operators could generally control the direction of stone movement.

In the empirical study, a sonographer using Doppler ultrasound and what is known as "twinkling artifact" visualized stones as small as 1 mm in the kidney of a porcine animal model. When pushing ultrasound was applied, these stones were seen on the real-time ultrasound display to jump up at ~1 cm/s. While in some embodiments pushing ultrasound exposure might result in thermal damage to tissue, no such damage was noted in the empirical study. The empirical study indicated that pushing ultrasound can be used to move stones within a collecting system in order to optimize rates of stone clearance.

It should be noted that while the present novel approach of moving kidney stones (or fragments thereof) using focused ultrasound represents an exemplary embodiment, the concepts disclosed herein can also be used to move other embedded objects, including, but not limited to, stones, fragments and dust located in any of the gall bladder, the salivary tract, and the biliary tract of a human or other mammal.

The following Figures illustrate various modes of detection of stones in accordance with the invention, in which like reference numerals indicate like components. These various modes of detection can be used either alone or in combination with each other and a voting algorithm or with the use of pushing ultrasound to facilitate stone clearance, as discussed above.

Figure 5:
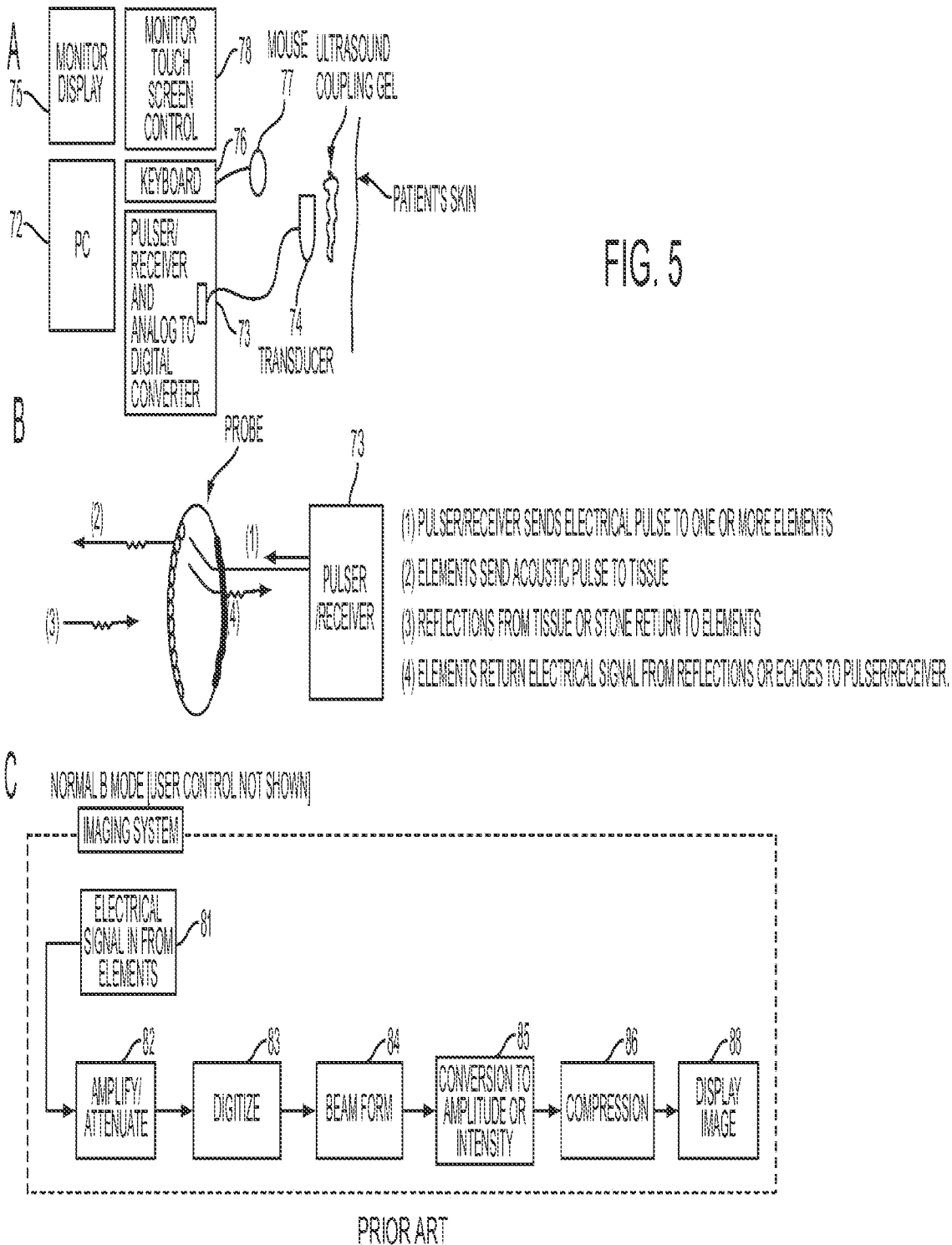

FIG. 5A is a schematic representation of a system suitable for use in the present invention comprising a CPU 72, a combined ultrasound pulser/receiver and analog to digital converter 73 operatively connected to a transducer 74, a monitor display 75, and various means for operator input and control such as keyboard 76, mouse 77, and monitor touch screen control 78, all of which are conventional in the computerized diagnostic arts. Transducer 74 can be used to apply detection and/or pushing ultrasound to a patient and to receive reflected ultrasound signals and transmit them back to CPU 72 for further processing as described more fully below, and as shown schematically in FIG. 5B.

FIG. 5C is a flowchart of a method and system 80 of the prior art using B-mode imaging ultrasound. Reflected ultrasound waves are received by the transducer elements 81, and are converted to electrical signals. The electrical signals pass through one or more attenuators and/or amplifiers, collectively indicated at 82, and the amplified and/or attenuated signals are then transmitted to analog-to-digital converter 83. From converter 83 the digitized signals pass to beam former 84, and then to converter 85 where the signals are converted to either amplitude or intensity. The converted are then transmitted to compression means 86, where their values which range over a large scale (e.g., 1-100000) are remapped to a smaller scale (e.g., 1-256) according to some defined algorithm. The compressed data are then displayed at display means 88.

Figure 6:
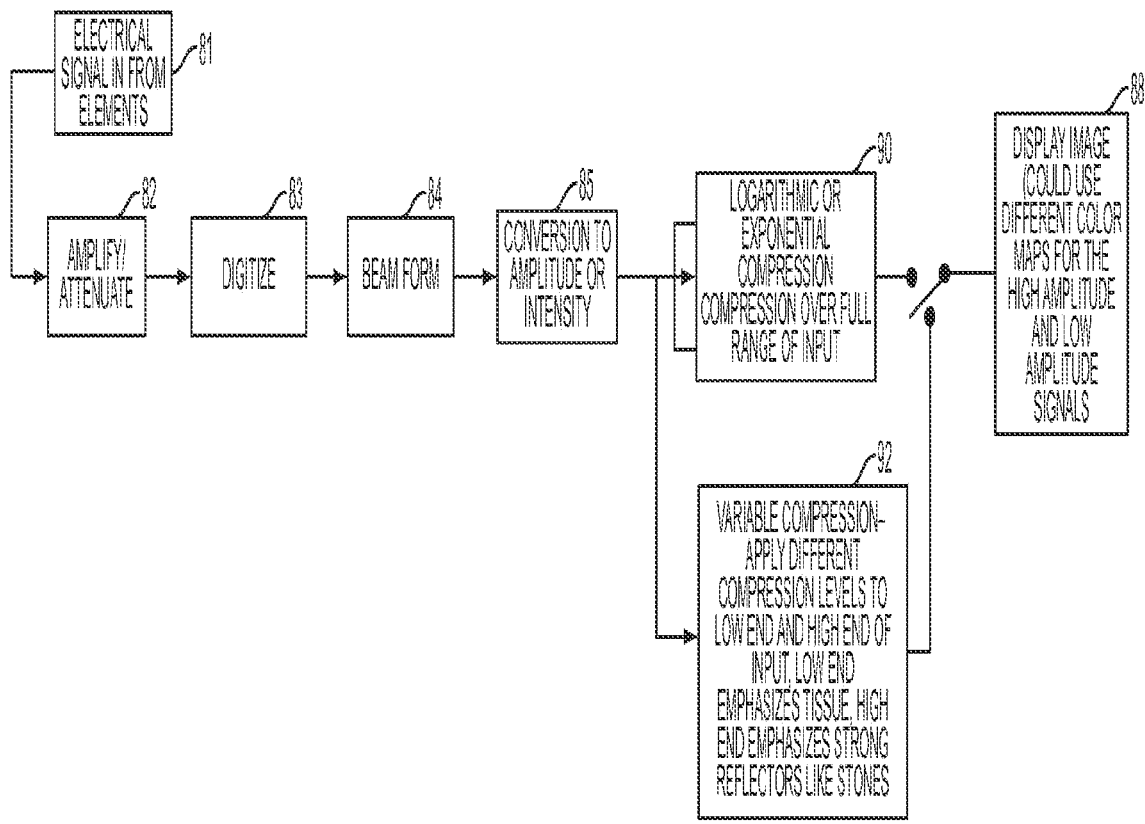
FIG. 6 is a flowchart of one embodiment of the present invention using B-mode ultrasound to preferentially identify and display an image of a stone relative to blood or tissue in which the reflected signals of greatest amplitude or intensity are selected and labeled with color on the display.

FIG. 6 is a flowchart of an embodiment of the invention using B-mode ultrasound and in which the more intense ultrasound signals reflected from a stone, especially in contrast to less intense signals from regions immediately adjacent to the stone, are preferentially selected or enhanced relative to the less intense ultrasound reflections from blood and tissue. This embodiment is based on the fact that stones normally appear brighter than tissue or blood on a B-mode ultrasound image because of the higher amplitude acoustic reflection from a stone, such that in this embodiment the reflected waves of higher amplitude are displayed in color to indicate the presence of a stone. In this embodiment, the data from converter 85 is subjected to one of two specific types of data compression. At compression means 90, the data are subjected to either logarithmic or exponential compression over the full range of the data input. At alternative compression means 92, the data are subjected to alternative compression schemes which magnify the differences between intense signals, wherein the low end magnification emphasizes tissue and the high end magnification emphasizes strong reflectors like stones, such that the mode of compression can be selected to emphasize stones. Those signals that reach a predetermined threshold of amplitude or intensity, typically about 95% of maximum, are then interpreted as strong signals reflected from a stone, such that the CPU can operate to preferentially add color to the display of the stone, or add one color to the high amplitude (or intensity) signals to indicate stone and a different color to the low amplitude (or intensity) signals to indicate tissue.

Figure 7:
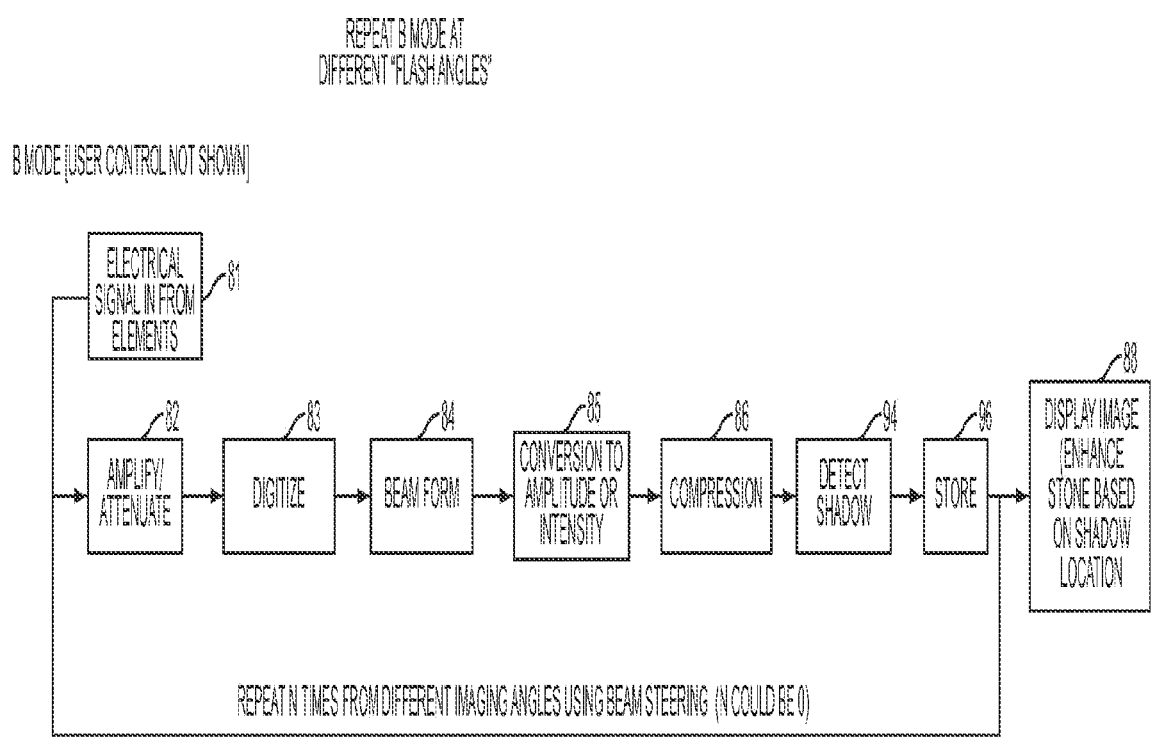
FIG. 7 is a flowchart of one embodiment of the present invention using B-mode ultrasound to preferentially identify and display an image of a stone relative to blood or tissue using the shadow created when B-mode ultrasound encounters a stone.

FIG. 7 is a flowchart of an alternative embodiment of the invention using B-mode ultrasound and in which the more intense ultrasound signals reflected from a stone, especially in contrast to less intense signals from regions immediately adjacent to the stone, are preferentially selected or enhanced relative to the less intense ultrasound reflections from blood and tissue. This embodiment relies on the ultrasound "shadows" generated when ultrasound is reflected from a stone, such the bright spot of the reflection is immediately proximal to the darker spot which represents the shadow on the distal side of the stone. The data is analyzed for this shadow artifact at data analyzer 94, wherein the stone is identified by the adjacency of the bright and dark spots. In a preferred embodiment, the B-mode ultrasound is reapplied at different exposure angles to confirm the presence of the shadow and therefore the presence of the stone. In addition, the ultrasound beam can be modified as is known in the art in other ultrasound applications, for example to a broad plane wave, called in the art a flash, to quickly image the whole field and enhance a shadow that can be obscured in a more focused imaging beam. Once identification of the stone is confirmed the information is optionally stored in data storage means 96 and the generated image of the stone is labeled or otherwise enhanced at display means 88 to indicate the presence of a stone to the operator.

Figure 8:
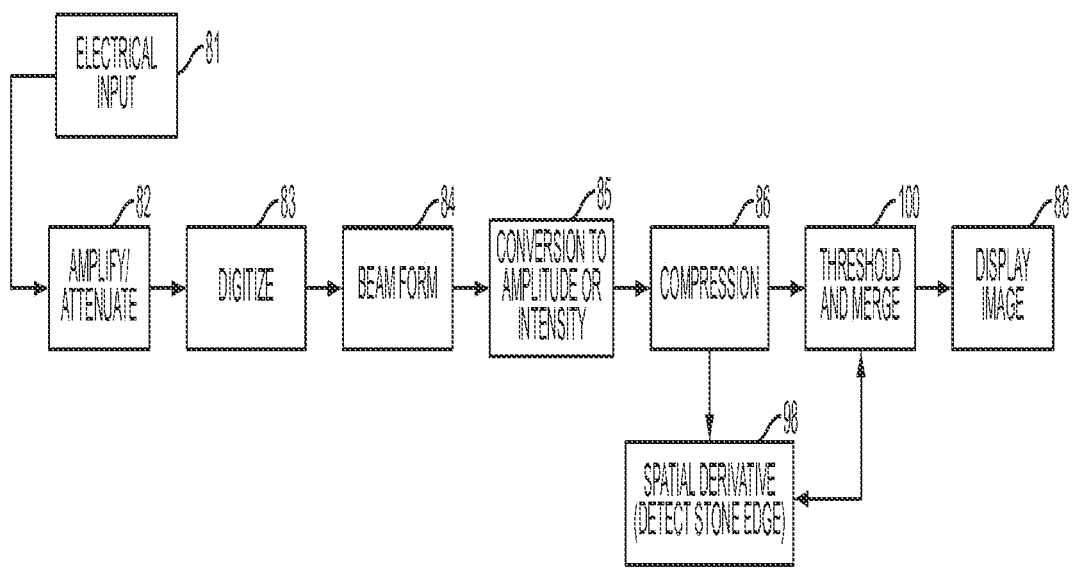
FIG. 8 is a flowchart of one embodiment of the present invention using B-mode ultrasound to preferentially identify and display an image of a stone relative to blood or tissue and using a spatial derivative of the data collected to determine the presence of a stone.

FIG. 8 is a flowchart of an alternative embodiment of the invention using B-mode ultrasound and in which the more intense ultrasound signals reflected from a stone, especially in contrast to less intense signals from regions immediately adjacent to the stone, are preferentially selected or enhanced relative to the less intense ultrasound reflections from blood and tissue in which an image is created from the spatial derivative of the intensity map, such that the highest derivatives indicate the location of the stone. Data from or before compression means 86 is processed at data analyzer 98 to take the spatial derivative, such that the abrupt change in brightness (high derivative) indicates the edge of a stone. These data are then merged with the compressed data to generate an image displayed at display means 88.

Figure 9:
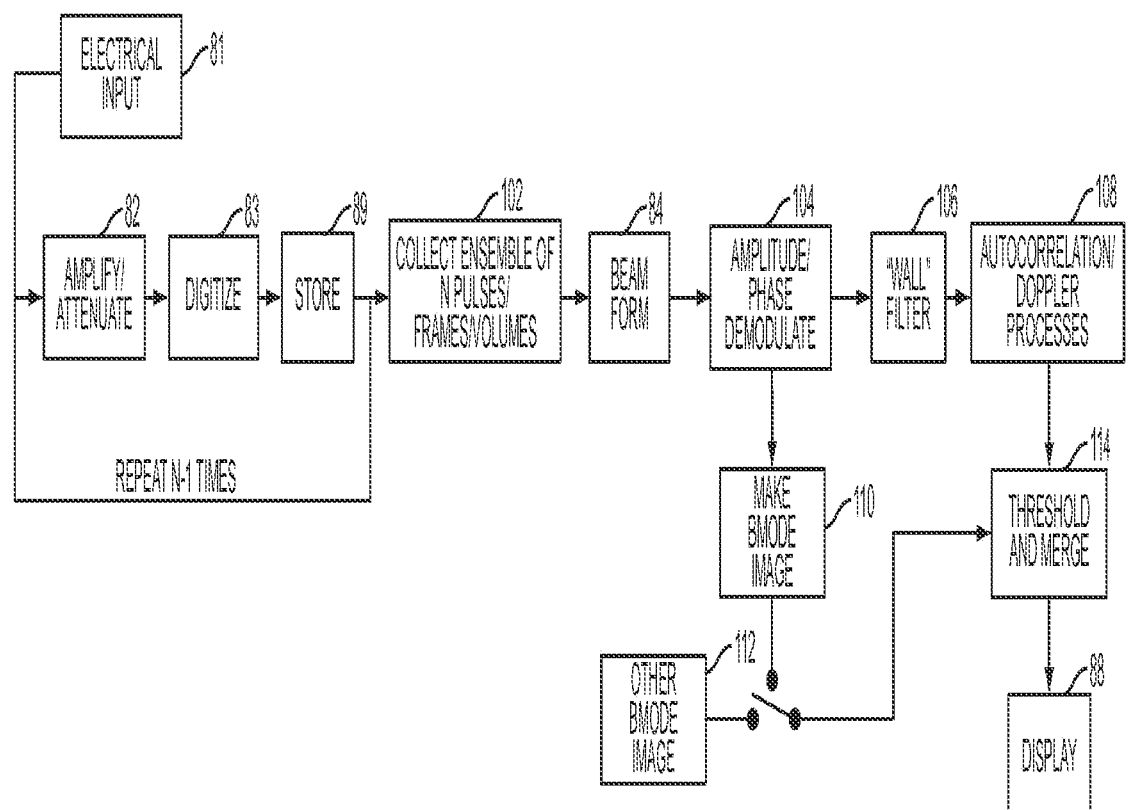
FIG. 9 is a flowchart of a system for Doppler ultrasound imaging in accordance with the prior art.

FIG. 9 is a flowchart illustrating standard prior art methods of Doppler ultrasound. Doppler ultrasound is applied to the subject, the reflected waves are amplified or attenuated and digitized, and the information is stored at storage means 89. This step may be repeated n−1 times to generate an ensemble of data at data collection means 102. The ensemble of data is beam-formed at 84. The data in beam form are then demodulated into phase and amplitude components at 104. As is known in the art, ultrasound that reflects off tissues such as vessel walls will have a higher amplitude than ultrasound that reflects off of blood. Also the tissue either is not moving or is moving very slowly compared to blood, so at this point in the processing the signals from tissue are lower frequency and the signals from blood are higher frequency. Therefore wall filter 106 removes the low frequency data from tissue, leaving only the data relating to the presence of blood. The filtered data are then processed by autocorrelation at 108 to optimize the indication of blood in the image at a predetermined threshold amplitude. A B-mode image which shows other pertinent features (i.e., anatomical structures) can be either generated from the demodulated data at 110 or obtained from a separate data source at 112. This B-mode image is then merged at 114 with the autocorrelated data from 108, such that a display is provided at 88 comprising both the B-mode image of the surrounding anatomy and the Doppler image of the blood.

In the prior art methods of processing Doppler data, the data are processed to eliminate signals having higher amplitudes, large discontinuities, outliers, and broad band twinkling effects, so that blood and tissue are more readily seen. In each of the following embodiments of the invention, the opposite approach is used, i.e., those signals that are generally discarded in prior art Doppler ultrasound systems are not only retained in the present invention but are accentuated relative to the signals reflected from blood and tissue, to more accurately identify the stones that generate such signals. Each of the embodiments of FIGS. 10-13 represents a different statistical approach to achieving this goal.

Figure 10:
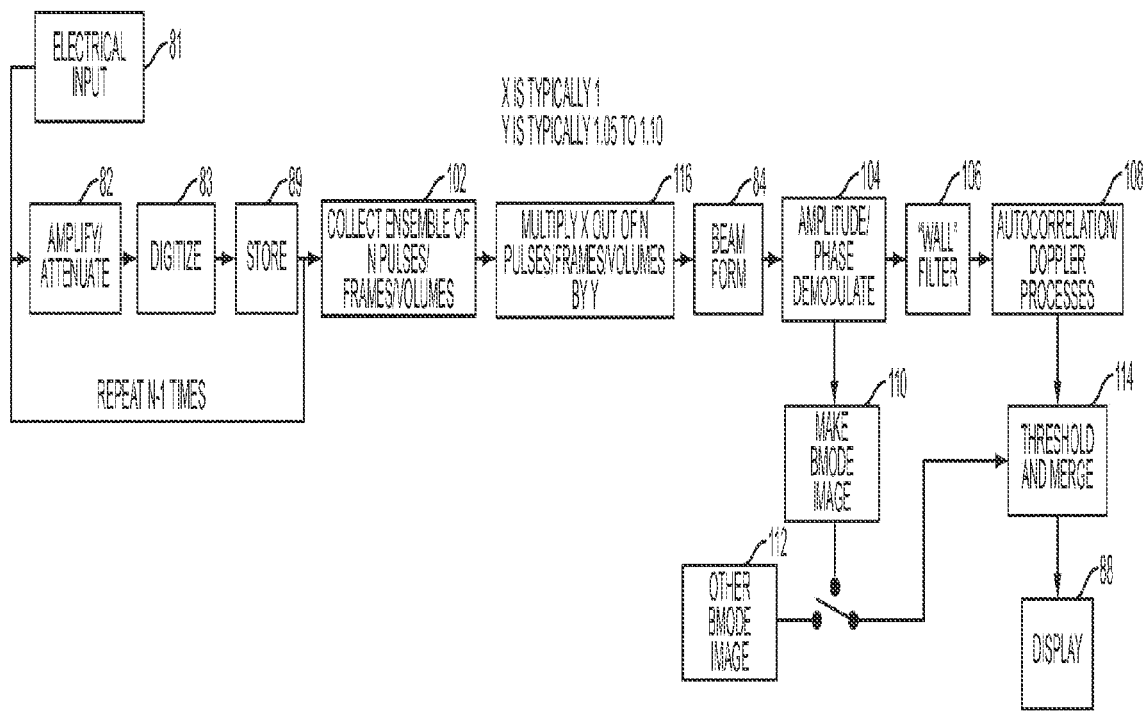
FIG. 10 is a flowchart of one embodiment of the present invention using Doppler ultrasound to preferentially identify and display an image of a stone relative to blood or tissue and wherein one or more units of pulses, frames or volumes in the ensemble is multiplied by a selected factor.

FIG. 10 is a flowchart of a modification of the method of FIG. 9 with the additional step at 116 of multiplying one or more of the data sets, also known as frames, in an ensemble by a selected factor. In one exemplary embodiment, raw data of fourteen frames is collected in an ensemble and one or more of the individual frames is multiplied by a factor of about 1.05-1.1, such that the amplitude of the data in that frame is amplified by about 5-10%. The reflections from the stones within each frame vary more greatly and in a more random way from frame to frame than do the reflections from tissue or blood. This manifests at a point in the Doppler processing as broadband frequency or noise compared to the low frequency from tissue and the narrow-band relatively high frequency from blood. The broadband frequency or high random variability from stones causes the twinkling artifact. The 5-10% amplification to one frame amplifies the variability among or between frames to further draw out the high variability signals from stones so as to be readily identified at display means 88, thereby providing a more sensitive means for detecting stones.

Figure 11:
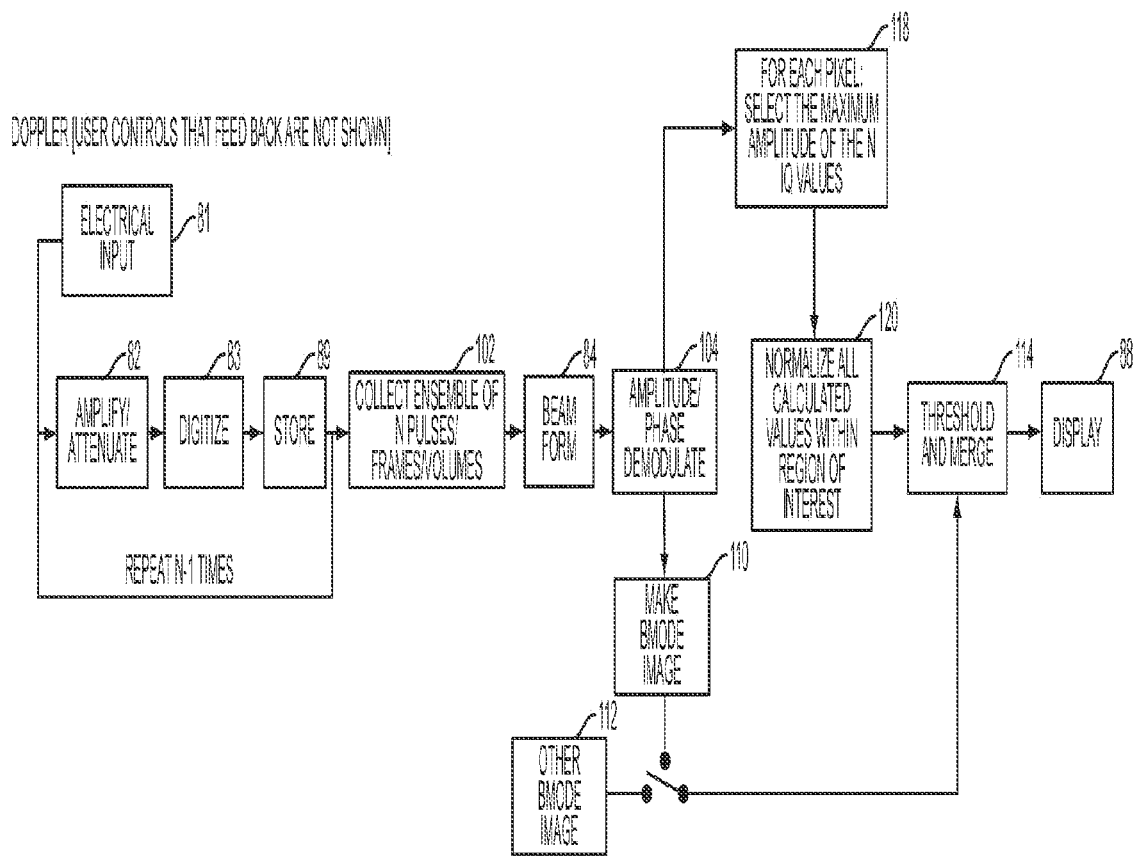
FIG. 11 is a flowchart of one embodiment of the present invention using Doppler ultrasound to preferentially identify and display an image of a stone relative to blood or tissue and relating to detection of large changes in amplitude among units of pulses, frames or volumes of an ensemble.

FIG. 11 is another alternative embodiment of the stone detection method of the invention using Doppler radiation and with the additional step of detecting relatively large changes particularly in amplitude, i.e., "outliers," within frames in the ensemble In one aspect of this embodiment of the invention, in place of a standard wall filter and autocorrelation the stone detection method is based on relatively large jumps of a single IQ pair in the Doppler ensemble for a pixel. This can be done in several ways that will be recognized by those skilled in the art of statistical data analysis. For example, in one embodiment, at each pixel the maximum amplitude is determined as max(signal IQ)−mean (signal IQ). In another mode, the z-score will be used to evaluate the data distribution, and the twinkling reflections are determined as outliers based on the number of standard deviations outside the expected range.

The selected values are normalized within the region of interest at step 120; these values are then merged with a B-mode image and displayed at display means 88.

Figure 12:
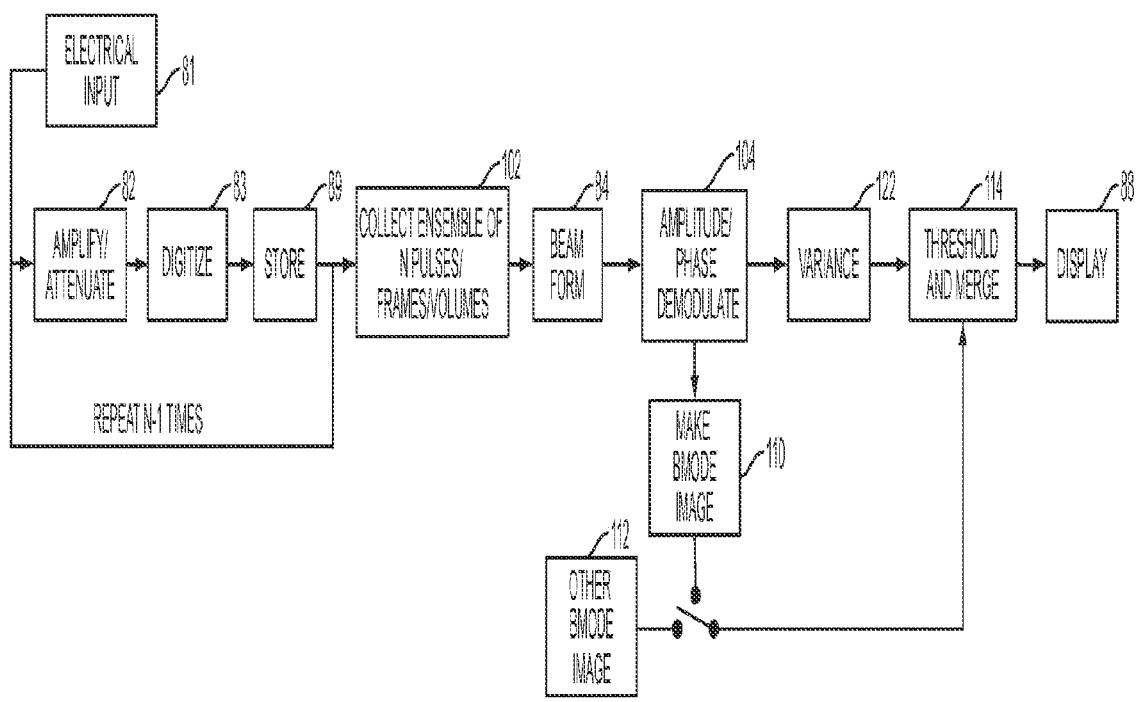
FIG. 12 is a flowchart of one embodiment of the present invention using Doppler ultrasound to preferentially identify and display an image of a stone relative to blood or tissue and relating to calculation of the variance of the signal.

FIG. 12 is a modification of the method of FIG. 11 wherein instead of a determination of outliers there is at 122 a statistical determination of the variance of the data, where variance according to its mathematical definition is determined as the amount of deviation left in the data after the mean is subtracted out. This statistical method retains signals such as twinkling artifacts that are not close to the mean of the data, such that these signals are accentuated at display means 88.

Figure 13:
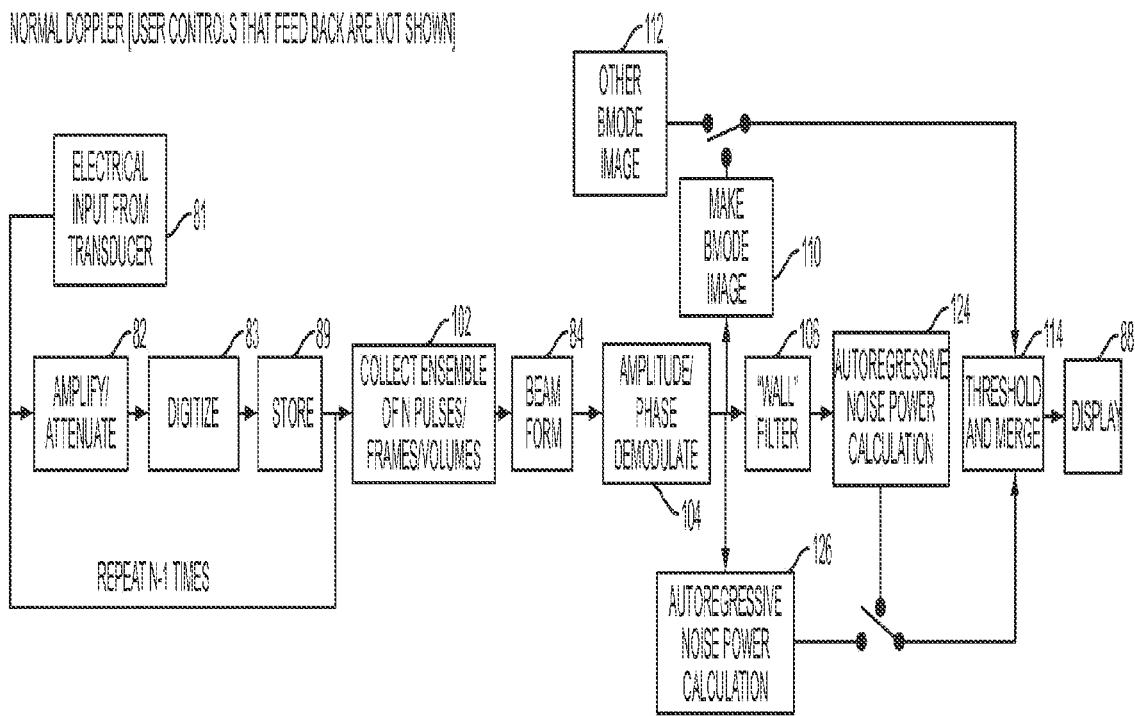
FIG. 13 is a flowchart of one embodiment of the present invention using Doppler ultrasound to preferentially identify and display an image of a stone relative to blood or tissue and relating to detection of the strength of the noise and not the signal from the autocorrelation, optionally with a wall filter.

FIG. 13 is a modification of the algorithm of FIG. 10 but in which an autoregression analysis is used rather than an autocorrelation of the Doppler data. This embodiment can be operated in two different modes. In one mode of operation of this embodiment, the demodulated data from step 104 is processed by a wall filter to remove data relating to reflections from tissue. The data is then subjected to a first or higher order autoregression analysis to identify coherent signals from blood flow. In the alternate mode of operation, no wall filter is used, but the data undergoes a second or higher order autoregression analysis at 126 to identify coherent signals from tissue and blood flow. In either mode of operation, the autoregression analysis suppresses coherent signals leaving only noise over a broad spectrum. The analyzed data is then subjected to a threshold determination such that the signals with the higher noise power are considered to be the twinkling signals and are displayed with the B-mode ultrasound image on the display 88.

Another aspect of the invention relates to a method for determining the output voltage and threshold level. In considering the distribution of the calculated twinklepower, as the output voltage for the system increases, the distribution of the non stone pixels shifts lower, while the stone pixels remain at the high end of the range. The threshold for display can be set at the high end of the non-stone distribution, but below the stone threshold. This method works because as the output voltage is increased, the tissue signal-to-noise ratio increases and is better filtered by the wall filter, while the effect that causes the stone to twinkle remains.

In one embodiment of one aspect of the invention, any one or more of image processing techniques such as 2D cross-correlation, phase correlation, and feature-edge detection are used to overlay color on the stone in the real-time, B-mode images and to assign a color to indicate the confidence in the identification of the stone.

In another embodiment the system can detect a moving stone, re-target the pushing ultrasound, and apply a new focused push pulse at that location.

It will be recognized by those skilled in the art that any combination of detection algorithms can be combined using a decision matrix to optimize the location of the stone. Also variations of the above methods will be recognized by those skilled in the art. For example, in any of the illustrated embodiments, the beam forming at 84 could be analog beam forming that would then occur prior to digitization. Beam forming also could occur within the ensemble collection loop. Similarly, in each of the foregoing embodiments the system makes a threshold determination as to which information to display at each pixel of display means 88, unless a multi-dimensional color map or semi-transparent layers are used. In the embodiments illustrated herein, the threshold determination is based on the B-mode power and the noise power. Those skilled in the art will recognize that such a threshold determination also could be made on the basis of traditional Doppler power, velocity, variance, higher order moments, or other information that can be obtained from the autoregression model.

It also will be appreciated that any of the detection methods of the present invention as illustrated in FIGS. 6-8 and 10-13 and described above can be practiced in conjunction with other aspects of this invention, in particular with other data analysis aspects of the invention, or with or without the use of pushing ultrasound to move a stone. The detection methods disclosed herein can be used either to display an image of a stone, or to provide an aural or other indication of the presence and/or location of a stone.

The system described in Example 1 above also was used to perform all the same experiments described in Example 2. The system was operated with the following parameters:

| | | |
|---|---|---|
| Push Pulse Frequency | 2.3 MHz | Dependent on transducer |
| Push Pulse length | 0.1 msec | Determined empirically |
| Push Pulse Frame rate | 15 frames/second | Could be increased if necessary |
| Push Pulse time | 1 second | Limited to prevent transducer damage |
| Charge Time | 3.0 msec | Determined empirically |
| Imaging time | 2.5 msec | Dependent on imaging depth |
| # of pushes/frame | 21 | Dependent on imaging time, push pulse, charge time and frame rate |
| Push Pulse Duty cycle | 3.15% | Total CLEAR time/duration of 1 frame |

Detection of the fragment was achieved using the imaging described above, B-mode ultrasound, and the twinkling artifact produced by the stones/fragments in Doppler mode ultrasound. In this empirical study, the same elements in the transducer were used for both imaging and pushing. Ultrasound and fluoroscopy showed the stones moving in real-time under the influence of the pushing ultrasound. Stones moved on the order of 1 cm/s away from the source, and several stones moved several centimeters down the ureter. It appeared that such movement was only induced when the stones/fragments were directly in the path of the focal beam, indicating that radiation pressure, as opposed to streaming, caused the motion. While ultrasound imaging and fluoroscopy were used independently in this study to track the initial position and motion of the stone/fragments being moved by the pushing ultrasound, other imaging modalities could be employed. Such imaging modalities include, without limitation, fluoroscopy, computed tomography (CT), low-dose stone protocol CT, B-mode ultrasound, magnetic resonance imaging (MRI), and Doppler ultrasound. When Doppler ultrasound is used the twinkling artifact may make the stones appear brightly colored in the image display. The methods and systems disclosed herein can be adapted to use the twinkling artifact to facilitate visualization of the stones for diagnosis and treatment.

EXAMPLE 2

Figure 14:
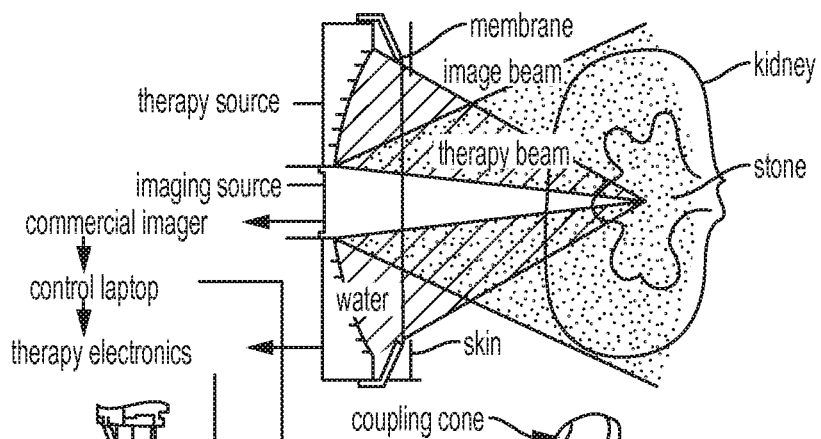
FIG. 14 is an illustration of a device used in the embodiment of Example 2 of this application.
Figure 14:
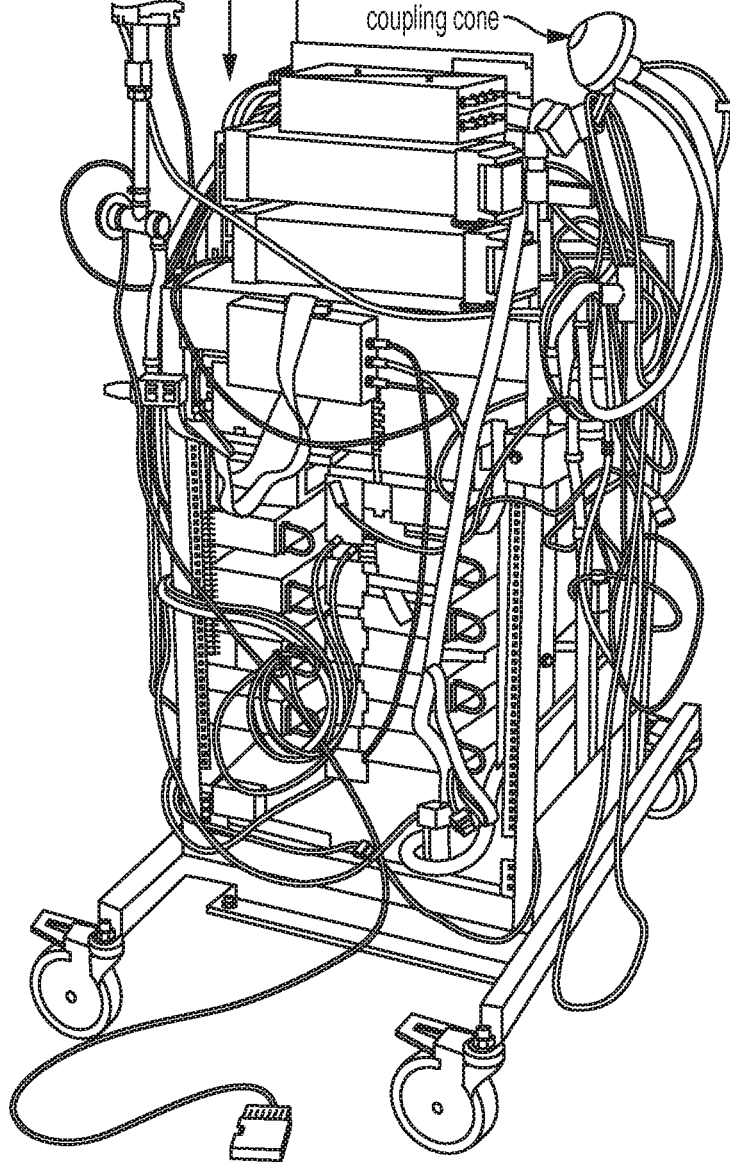

The system used in the Examples is shown in FIG. 14 in which (a) is a diagram and (b) is a photograph of the ultrasound system. It consisted of a 6 cm dia., 2 MHz, eight element annular array curved to a natural focus of 6 cm (Sonic Concepts model H-106, Bothell, Wash.). The eight elements were excited by the synchronized outputs of 8 signals from an SC-200 radiofrequency synthesizer (Sonic Concepts, Bothell, Wash.) and amplified by eight 100 W amplifiers (Icom IC-706MKIIG, Bellevue, Wash.). A laptop computer controlled the timing of the excitation of each element, which allowed the focal depth to be varied from 4.5-8.5 cm. The computer also collected the image from the ultrasound imaging system (HDI-5000, Philips/ATL, Bothell, Wash.) and overlaid on the image the user selected focusing depth so the user could visually align the stone at the focus. The probe of the imager (P4-2) looked through the aperture of the therapy array and was within a water-filled coupling head much like a shock wave lithotripter but smaller and held in the hand of the user. The electronics and probe with the longer coupling cone are shown in the photograph. The ultrasound imager is not shown. A footswitch switch turned the focused ultrasound such that it was on for about 50 ms and off for about 50 ms while the switch was closed. Interference obscured the imaging while the focused ultrasound was on but properly synchronized pulsing permitted the half of the image containing the stone to remain obscured. Total exposure in a burst of pulses was 1-4 s, and no more than 10 bursts were used to move one stone. The acoustic beam is shaped as an hourglass with the greatest energy concentration and highest pressures in the narrow focus region. The region over which the pressures are within half of the peak pressure is only 1 cm long and about 1 mm wide. Time-averaged acoustic intensities, measured in water and derated to the 6.5 cm penetration depth in tissue were 250, 500, and 1000 W/cm$^2$.

All animal studies were acute, and animal research procedures were approved by the University of Washington IACUC. Twelve common domestic female pigs (age 5 months and 50-60 kg) underwent induction of general anesthesia, had their flank regions shaved and depilated, and were secured to the operation room table. In six pigs, artificial stones (radio-opaque glass/metal beads 3 and 5 mm in diameter) and human urinary stones (cystine, calcium oxalate monohydrate, or calcium hydrogen phosphate dihydrate, 1-8 mm) were endoscopically placed into the lower pole using retrograde ureteroscopy, retrograde percutaneous nephrolithomy or open surgical access and canalization of the ureter. A retrograde pyelogram was performed to outline the porcine collecting system. Prior the treatment with focused ultrasound, stone position was visually confirmed endoscopically and fluoroscopically. Most stones were placed in the lower pole but many were placed in upper pole calyces.

Both kidneys were accesses through open surgery in the other six anesthetized pigs. A longer coupling cone was added the array to place the focus 0.5-1 cm beyond the end of the cone. The abdomen was filled with saline to ensure coupling, and the cone was placed in direct contact with the kidney. Five regions on each kidney were targeted, and the surface location marked with ink. Control regions of the kidney received no ultrasound exposure. Other regions received two minute total exposure at 50% duty cycle at time averaged intensities 325 and 1900 W/cm$^2$. The pigs were sacrificed, and the kidneys were harvested. Both kidneys were freshly sectioned for gross examination, and samples embedded for histological analysis. Microscopic examination was performed using serial sections stained with hematoxylin and eosin (H&E) and nicotinamide adenine dinucleotide-diaphorase (NADH-d). Any signs of thermal or mechanical injury to the renal parenchyma were assessed by observers blinded to the exposure conditions.

Figure 15:
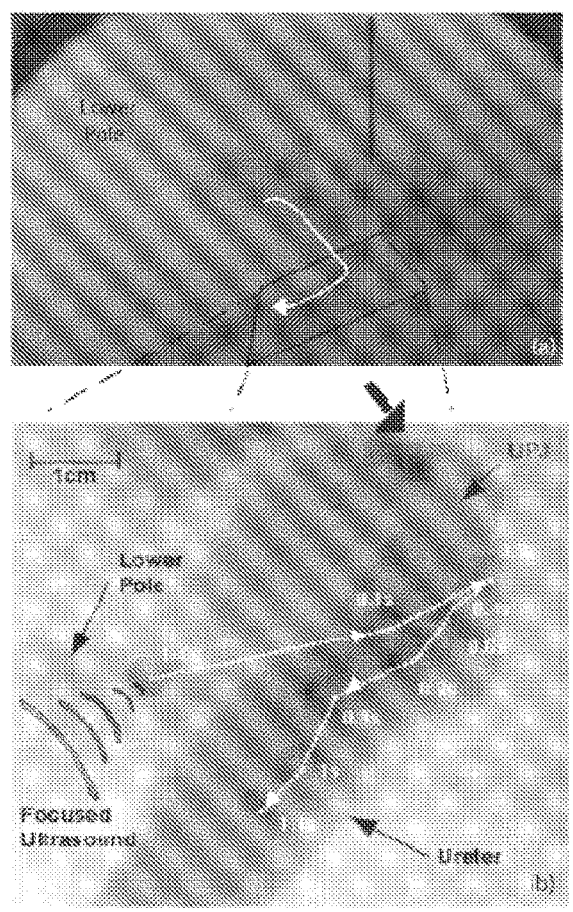
FIG. 15 is a representative image of ultrasonic propulsion of a stone in accordance with Example 2 of this application.

FIG. 15 shows super-imposed frames of a fluoroscopic movie tracking the ultrasonic expulsion of a bead. The fluoroscopic image shows the 5-mm bead moved roughly 3 cm in 1.3 s traveling from the lower pole through the UPJ into the ureter. A single ultrasound burst pushed the 5-mm bead from the lower pole to the UPJ where it is bounced and fell into the canalized ureter. The beads are denser and much more radio-opaque and therefore easier to observe in the fluoroscopic images than the human kidney stones that were used. The bead moved several centimeters in 1.1 s. The duration of the ultrasound burst was only 1 s and more importantly the ultrasound energy is concentrated into a region only 1 cm long. The impulsive push of the stone was sufficient to make the bead move beyond the ultrasound focus. Stones or beads were moved to the renal pelvis and ureteropelvic junction (UPJ) in all six pigs. No more than ten minutes per stone were required, and total exposures to focused ultrasound were shorter than two minutes. Average velocity of stone movement was about 1 cm/s and stones traveled on average about 1 cm with each effective 1 s propulsion pulse. Most of the effort was visualizing the stone at an appropriate angle to push it into a fluid space toward the UPJ. Angles of focus that were parallel to the axis of the infundibulum resulted in larger displacement of the stone. Stone motion was not observed at all angles of focused ultrasound delivery, but often if stones were pushed toward a tissue interface the stone ricocheted in a direction along the interface. Larger fluid spaces made propulsion easier. Stones were repositioned at all acoustic intensities used: previous in vitro experiments were not successful with lower intensities. It was not observed that a stone was suddenly made to move simply by increasing the power or that stones moved faster with more power. We concluded that the difficulty in moving these stones was primarily due to alignment of the narrow focus on the stone at an appropriate angle.

Figure 16:
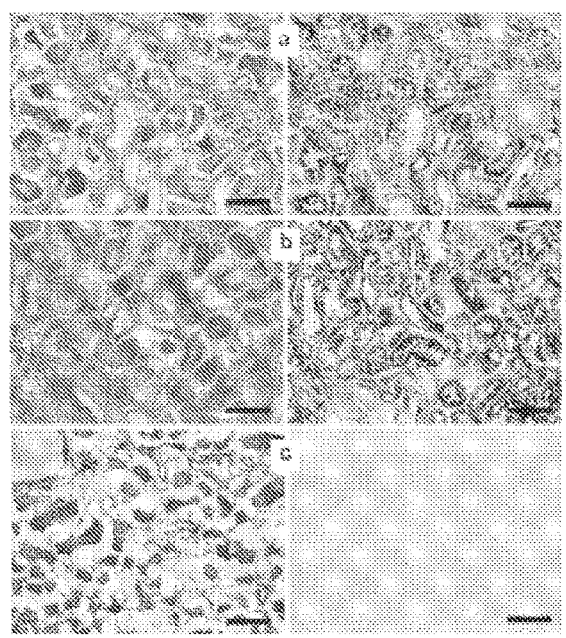
FIG. 16 is a representative histology slide from a control, and exposure to 325 W/cm$^2$ and exposure to 1900 W/cm$^2$ of the sample of Example 2 of this application.

FIG. 16 shows a representative histology slide from a control, and exposure to 325 W/cm² and exposure to 1900 W/cm². Specifically, the views are hematoxylin and eosin and nicotinamide adenine dinucleotide stained sections of porcine kidney (a) not exposed to ultrasound (b) exposed to levels used in the ultrasonic propulsion of stones, and (c) exposed to levels above those used for stone propulsion. Thermal injury is shown in image (c). The bar represents 100 μm. Control and the sample from the 325 W/cm² exposure are similar and show no apparent injury. The sample from the 1900 W/cm² exposure contains damaged regions consistent with thermal coagulation, as evidenced by shrinkage of the cells and increased intensity of eosinophilic staining. The NADH-d stained serial section confirmed thermal damage in the 1900 W/cm² exposure sample as indicated by the lack of staining. None of the three control samples or five samples from the 325 W/cm² exposure showed any evidence of injury thermal or otherwise. Six of the seven samples from the 1900 W/cm² exposure showed thermal injury, but the lesion created was localized to within 1 cm in its longest dimension. Thus, a threshold for injury exists, but it appears to be above the level required to move stones.

Although the concepts disclosed herein have been described in connection with the preferred form of practicing them and modifications thereto, those of ordinary skill in the art will understand that many other modifications can be made thereto. Accordingly, it is not intended that the scope of these concepts in any way be limited by the above description.

What is claimed is:

1. A method for applying a force to a stone in a living body, comprising generating one or more pulses of ultrasound radiation to push the stone in vivo without fragmenting the stone, the ultrasound radiation imparting a transfer of momentum to the stone resulting in displacement of the stone without causing thermal or mechanical damage to surrounding tissue, wherein the one or more pulses have a spatial peak temporal average intensity ($I_{SPTA}$) between 3 and 325 watts per square centimeter (325 W/cm² > $I_{SPTA}$ > 3 W/cm²), wherein the one or more pulses have an oscillation frequency (f) within a range of about 0.25 MHz to 5 MHz, wherein the one or more pulses induce a peak negative pressure amplitude (P) that is defined by: $|P|<8\sqrt{f}$, and wherein the one or more pulses have a duty cycle of greater than about 1% and less than 100%.

2. The method of claim 1, wherein the one or more pulses have a spatial peak temporal average intensity greater than about four watts per square centimeter ($I_{SPTA}$ > 4 W/cm²).

3. The method of claim 1, wherein the one or more pulses each have a pulse duration of greater than 2.2 ms.

4. The method of claim 1, wherein the one or more pulses each have a pulse duration of about 50 ms.

5. The method of claim 1, wherein the stone is exposed to the one or more pulses for a cumulative time of less than about two minutes.

6. The method of claim 5, wherein the one or more pulses are generated within a continuous time period of less than about ten minutes.

7. The method of claim 1, wherein the one or more pulses each include an ultrasound wave oscillating at a frequency that is greater than or equal to 0.25 MHz and less than or equal to 1 MHz.

8. The method of claim 1, wherein the one or more pulses each include an ultrasound wave oscillating at a frequency that is greater than or equal to 1 MHz and less than or equal to 5 MHz.

9. The method of claim 1, wherein the one or more pulses each include an ultrasound wave oscillating at a frequency of about 2.3 MHz.

10. The method of claim 1, wherein the one or more pulses each include at least 5 oscillation cycles of an ultrasound wave.

11. The method of claim 1, wherein the one or more pulses each include at least 10 oscillation cycles of an ultrasound wave.

12. A non-transitory computer readable medium storing instructions that, when executed by an ultrasound device, cause the ultrasound device to perform functions for applying a force to a stone in a living body, the functions comprising generating one or more pulses of ultrasound radiation to push the stone in vivo without fragmenting the stone, the ultrasound radiation imparting a transfer of momentum to the stone resulting in displacement of the stone without causing thermal or mechanical damage to surrounding tissue, wherein the one or more pulses have a spatial peak temporal average intensity ($I_{SPTA}$) between 3 and 325 watts per square centimeter (325 W/cm² > $I_{SPTA}$ > 3 W/cm²), wherein the one or more pulses have an oscillation frequency (f) within a range of about 0.25 MHz to 5 MHz, wherein the one or more pulses induce a peak negative pressure amplitude (P) that is defined by: $|P|<8\sqrt{f}$, and wherein the one or more pulses have a duty cycle of greater than about 1% and less than 100%.

13. The non-transitory computer readable medium of claim 12, wherein the one or more pulses have a spatial peak temporal average intensity greater than about four watts per square centimeter ($I_{SPTA}$ > 4 W/cm²).

14. The non-transitory computer readable medium of claim 12, wherein the one or more pulses each have a pulse duration of greater than 2.2 ms.

15. The non-transitory computer readable medium of claim 12, wherein the one or more pulses each have a pulse duration of about 50 ms.

16. The non-transitory computer readable medium of claim 12, wherein the stone is exposed to the one or more pulses for a cumulative time of less than about two minutes.

17. The non-transitory computer readable medium of claim 16, wherein the one or more pulses are generated within a continuous time period of less than about ten minutes.

18. An ultrasound device comprising:
   a processor;
   an ultrasound transducer; and
   a non-transitory computer readable medium storing instructions that, when executed by the processor, cause the ultrasound device to perform functions for applying a force to a stone in a living body, the functions comprising:
      generating one or more pulses of ultrasound radiation to push the stone in vivo without fragmenting the stone, the ultrasound radiation imparting a transfer of momentum to the stone resulting in displacement of the stone without causing thermal or mechanical damage to surrounding tissue, wherein the one or more pulses have a spatial peak temporal average intensity ($I_{SPTA}$) between 3 and 325 watts per square centimeter (325 W/cm$^2$>$I_{SPTA}$>3 W/cm$^2$), wherein the one or more pulses have an oscillation frequency (f) within a range of about 0.25 MHz to 5 MHz, wherein the one or more pulses induce a peak negative pressure amplitude (P) that is defined by: $|P|<8\sqrt{f}$, and
   wherein the one or more pulses have a duty cycle of greater than about 1% and less than 100%.

19. The ultrasound device of claim 18, wherein the one or more pulses each include an ultrasound wave oscillating at a frequency that is greater than or equal to 0.25 MHz and less than or equal to 1 MHz.

20. The ultrasound device of claim 18, wherein the one or more pulses each include an ultrasound wave oscillating at a frequency that is greater than or equal to 1 MHz and less than or equal to 5 MHz.

* * * * *